United States Patent [19]

Archibald

[11] Patent Number: 4,673,390
[45] Date of Patent: Jun. 16, 1987

[54] MULTIPLE SOLUTION IV SYSTEM

[75] Inventor: G. Kent Archibald, White Bear Lake, Minn.

[73] Assignee: Minnesota Mining & Manufacturing Company, St. Paul, Minn.

[21] Appl. No.: 676,009

[22] Filed: Nov. 29, 1984

[51] Int. Cl.$^4$ .............................................. A61M 5/14
[52] U.S. Cl. ...................................... 604/81; 604/249; 604/250; 251/9; 251/68; 137/595; 128/DIG. 13
[58] Field of Search .................................. 604/80–83, 604/30, 31, 34, 65–67, 245–247, 248–250, 84–86, 28, 29; 128/DIG. 12, DIG. 13; 251/4, 6, 7, 9, 67, 68, 74; 137/636.1, 595

[56] References Cited

U.S. PATENT DOCUMENTS

| | | |
|---|---|---|
| Re. 16,251 | 1/1926 | Schellberg . |
| 790,353 | 5/1905 | Estlingen ............................. 604/34 |
| 1,683,723 | 9/1928 | Myres . |
| 2,866,457 | 12/1958 | Moore ................................. 128/214 |
| 3,895,649 | 7/1975 | Ellis ..................................... 137/595 |
| 4,094,318 | 6/1978 | Burke et al. ......................... 604/81 |
| 4,114,617 | 9/1978 | Turner et al. ....................... 128/214 |
| 4,137,940 | 2/1979 | Faisandier ................. 128/DIG. 13 |
| 4,256,240 | 5/1981 | Jenkins ................................ 128/214 |
| 4,316,460 | 2/1982 | Genese et al. ...................... 128/214 |
| 4,324,238 | 4/1982 | Genese et al. ...................... 128/214 |
| 4,391,598 | 7/1983 | Thompson ............................ 604/65 |
| 4,397,642 | 8/1983 | Lamadrid ............................ 604/245 |
| 4,425,116 | 1/1984 | Bilstad et al. ......................... 604/34 |
| 4,430,074 | 2/1984 | Mooring ............................... 604/81 |
| 4,512,764 | 4/1985 | Wunsch ................................ 604/80 |
| 4,524,802 | 6/1985 | Lawrence et al. .................... 604/34 |
| 4,533,347 | 8/1985 | Deckert ................................ 604/81 |

FOREIGN PATENT DOCUMENTS 1130107  6/1955  France ................................... 251/9

Primary Examiner—Dalton L. Truluck
Assistant Examiner—Mario Constantino
Attorney, Agent, or Firm—Kinney & Lange

[57] ABSTRACT

A multiple solution IV administration system includes a plurality of IV fluid sources which are connected by flexible tubing to the inlet of an IV pump. A sequence valve suspended from the tubing selectively pinches off all but one tube so that one source at a time is connected to the inlet. The sequence valve is controlled as a function of the accumulated volume pumped by the pump for each fluid and a stored volume limit for that fluid. When the accumulated volume of one IV fluid reaches its volume limit, the sequence valve is changed to connect a different source to the inlet of the IV pump.

6 Claims, 12 Drawing Figures

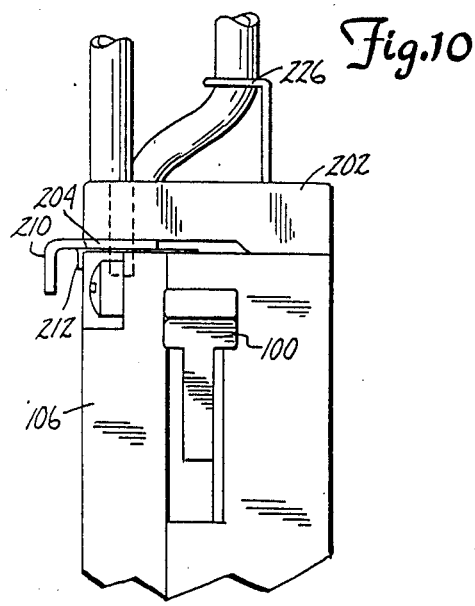
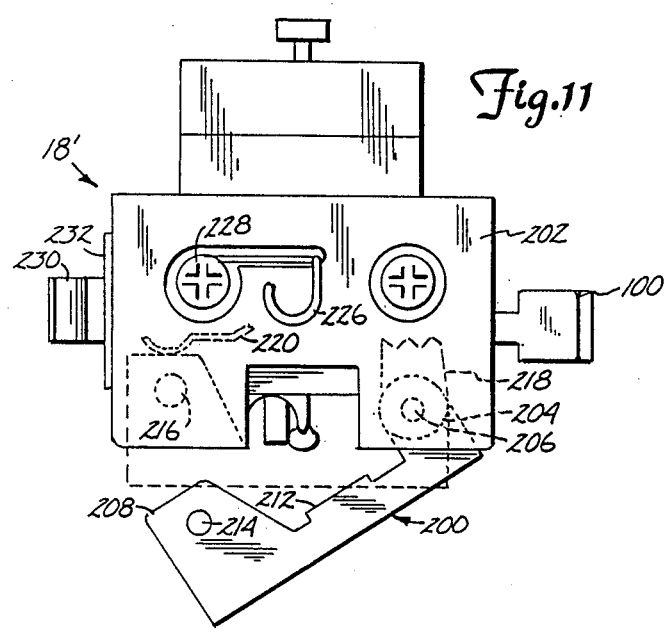
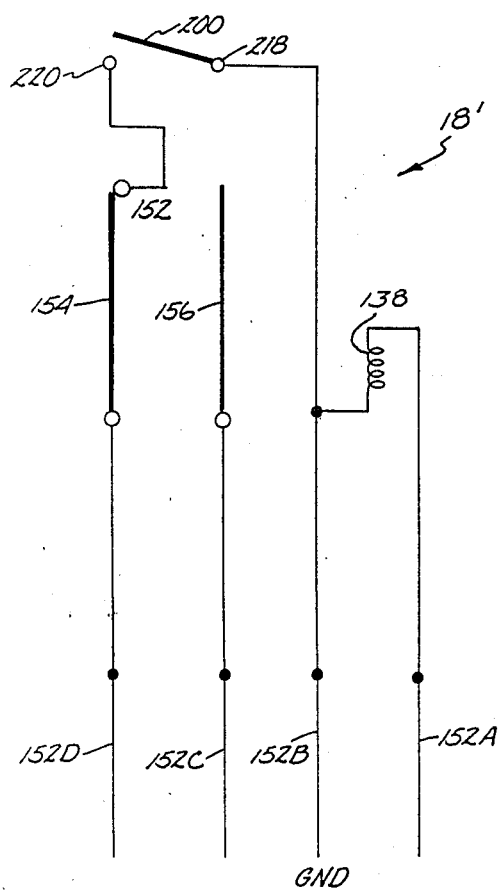

MULTIPLE SOLUTION IV SYSTEM

BACKGROUND OF THE INVENTION

1. Reference to Copending Application

Reference is made to a copending application by G. K. Archibald and F. Slaker entitled "Sequence Valve for Piggyback IV Administration" filed on even date with this application and assigned to the same assignee.

2. Field of the Invention

The present invention relates to administration of intravenous (IV) fluid. In particular, the present invention is an IV administration system which supplies multiple IV solutions or medications at predetermined intervals to a patient.

3. Description of the Prior Art

It is quite common in IV therapy to give a patient a primary solution and one or more secondary solutions or medications. The secondary (or "piggyback") medication is usually given several times a day. An example is when a patient is on antibiotics. It is desirable to have an IV pump and a sequencing valve that administers the primary and secondary solutions sequentially.

In the past, there have been IV pump systems which allow two fluids to be administered. In these systems, the secondary medication is pumped until the secondary container goes empty, and then the pump switches to the primary fluid. An example of this type of system is shown in U.S. Pat. No. 4,451,255. This proves to be a substantial burden to hospital personnel, particularly where the secondary medication is required several times a day. With the prior art systems, the medical personnel must change secondary medication bags several times each day.

SUMMARY OF THE INVENTION

The present invention is an improved IV administration system which has a valve which is suspended from and which acts on flexible tubing between the inlet of an IV control device (such as an IV pump or controller) and a plurality of sources of different IV fluids. The valve operates in response to a valve control signal by constricting all but one tube to selectively connect one of the sources to the inlet of the IV pump.

In the present invention, control means located with the IV control device provides the valve control signal to the valve means after a predetermined volume of one of the IV fluids is pumped by the IV control device. By monitoring operation of the IV control device, the control means controls operation of the valve means to switch from one source to another when the predetermined volume of IV fluid from the one source has been pumped.

With the present invention, therefore, all of the medication for a day or more may be contained in one large bag, as opposed to smaller secondary bags that run dry after each delivery of secondary medication. Since the cost of large versus small bags is essentially the same, the system of the present invention achieves significant cost savings by reducing the number of bags which are used, and by reducing the number of times that the medical personnel must change bags.

BRIEF DESCRIPTION OF THE DRAWINGS

FIGS. 9 and 10 are partial left and right side views of the sequence valve of FIG. 8.

FIG. 11 is a top view of the sequence valve of FIG. 8 with the tube retainer pivoted to its open position.

FIG. 12 is an electrical schematic diagram of the sequence valve of FIG. 8.

DETAILED DESCRIPTION OF THE PREFERRED EMBODIMENTS

Figure 1:
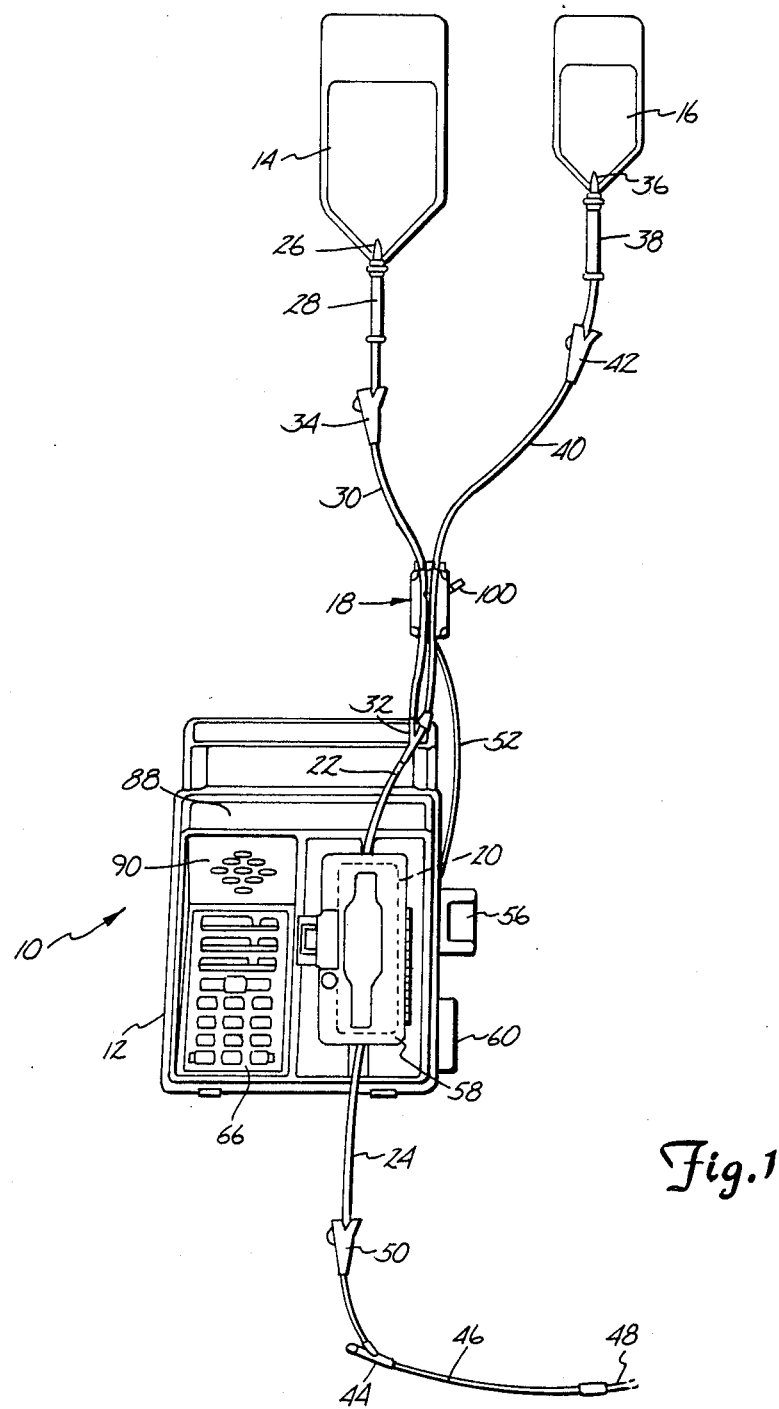
FIG. 1 is a partially schematic diagram of a preferred embodiment of the IV administration system of the present invention.

In the preferred embodiment shown in FIG. 1, IV administration system 10 includes IV pump 12, which pumps fluid from primary solution bag 14 or secondary (or piggyback) solution bag 16, to a patient (not shown). Sequence valve 18 is connected between bags 14 and 16 and pump 12 to select one of the bags 14 and 16 for connection to pump 12.

In the particular embodiment shown in FIG. 1, pump 12 is an IV pump such as the AVI GUARDIAN 400 pump manufactured by applicant's assignee AVI, inc. Pumps of this general type (which are described in U.S. Pat. No. 4,236,880) use a disposable multiple rolling diaphragm pumping chamber 20 which is inserted into pump 12. Pumping chamber 20 has an inlet tubing 22 connected at its inlet end, and an outlet tubing 24 at its outlet end. A drive mechanism within pump 12 causes relative movement of two of the rolling diaphragms of pumping chamber 20 and the operation of two valves to cause fluid to be pumped from inlet tubing 22 through pumping chamber 20 and out through outlet tubing 24 to the patient.

In the embodiment shown in FIG. 1, disposable multiple rolling diaphragm pumping chamber 20, inlet tubing 22 and outlet tubing 24 form a part of a disposable IV administration set which also includes primary spike 26, primary drip chamber 28, primary tubing 30, proximal Y connector 32, primary roller clamp 34, secondary spike 36, secondary drip chamber 38, secondary tubing 40, secondary roller clamp 42, distal Y connector 44, distal tubing 46, needle 48, and distal roller clamp 50.

Primary spike 26 is inserted into the lower end of primary bag 14, and is connected to the upper end of primary drip chamber 28. The lower end of primary drip chamber 28 is connected by primary tubing 30 to one leg of proximal Y connector 32.

Similarly, secondary spike 36 is inserted into the lower end of secondary bag 16 and is connected to the upper end of secondary drip chamber 38. The lower end of secondary drip chamber 38 is connected through secondary tubing 40 to the second leg of proximal Y connector 32. The third leg of Y connector 32 is connected to inlet tubing 22.

Primary tubing 30 and secondary tubing 40 pass through sequence valve 18, and at least one (preferably primary tubing 30) supports sequence valve 18. In the preferred embodiment of the present invention, sequence valve 18 is a light-weight, solenoid actuated device which initially pinches off primary tubing 30 to prevent flow from primary bag 14 while permitting flow from secondary bag 16 to pumping chamber 20. In response to a valve control signal received from pump 12 through multiconductor cable 52, sequence valve 18 switches so that secondary tubing 40 is pinched off and primary tubing 30 is unobstructed. When secondary tubing 40 is unobstructed and primary tubing 30 is pinched off, secondary (piggyback) bag 16 is connected to inlet tubing 22, and pump 12 pumps the secondary medication from piggyback bag 16 to the patient. Conversely, when secondary tubing 40 is pinched off and primary tubing 30 is unobstructed, the primary solution is pumped from the primary bag 14 to the patient by IV pump 12.

At the outlet end, outlet tubing 24 is connected through distal Y connector 44 to distal tubing 46. At the end of distal tubing 46 is needle 48, which is inserted into a vein of the patient. Distal Y connector 44 has another leg which is normally closed, but which allows the insertion of a syringe needle to introduce medication directly into distal tubing 46 as fluid is being pumped to the patient.

Roller clamps 34, 42 and 50 are used by medical personnel during the installation of the IV administration set into pump 12, during initial set-up, and during removal of the IV administration set.

Figure 2:
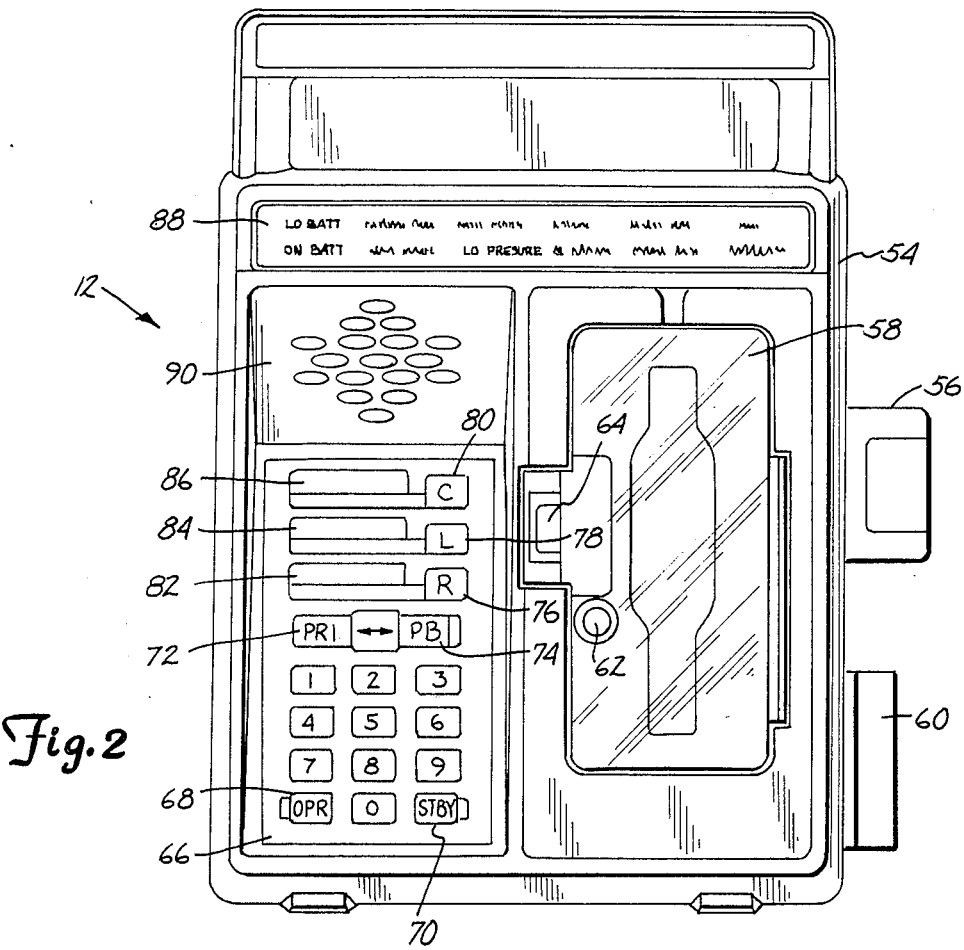
FIG. 2 is a front view of the IV pump of FIG. 1.

FIG. 2 shows a front view of pump 12. Pump 12 includes a housing 54 which contains the electrical control circuitry and the mechanical portions of the pump which interact with disposable pumping chamber 20. Pump 12 is supported on an IV stand or pole (not shown) by pole clamp 56. Door 58 covers a receptacle into which disposable pumping chamber 20 is inserted. In the embodiment shown in FIG. 2, the opening of door 58 requires operation of the three separate devices: load control handle 60, door lock 62, and door latch 64. During normal operation, when the IV administration set is installed with pumping chamber 20 within the receptacle of pump 12, door 58 is closed as shown in FIG. 2.

In the lower left corner of the front of pump 12 is control panel 66, which includes a keyboard formed by numerical key pads ("0" through "9"), operate key pad (OPR) 68, standby key pad (STBY) 70, PRIMARY key pad 72, PIGGYBACK key pad 74, RATE key pad 76, volume limit (LIMIT) key pad 78, and volume infused clear (CLEAR) key pad 80. Control panel 66 also includes three digital displays: rate display 82, volume limit display 84, and volume infused display 86.

Pump 12 also includes indicator panel 88, (which provides visual indication of different error or alarm conditions), and audio alarm annunciator 90.

Figure 3:
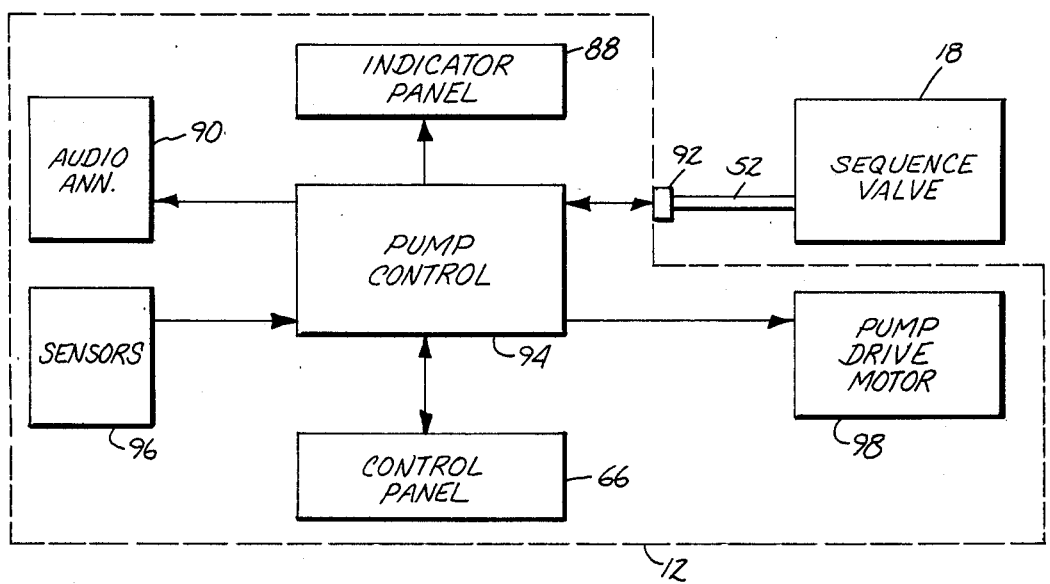
FIG. 3 is an electrical block diagram of the system of FIG. 1.

FIG. 3 is an electrical block diagram of pump 12 and sequence valve 18, which are connected together by multiconductor able 52 and connector 92 Sequence valve 18 receives a valve control signal from pump 12, and provides a valve state signal, which indicates which fluid line (primary tubing 30 or secondary tubing 40) is occluded.

The operation of pump 12 is controlled by pump control 94, which in preferred embodiments includes a microcomputer, together with associated memory, timing and clock circuitry and appropriate interface circuitry. Pump control 94 receives input signals from control panel 66, from sensors 96 (which sense various operating conditions or parameters such as output pressure, air bubbles in the IV administration set, empty bags and opening of door 58), and from sequence valve 18. Pump control 94 provides outputs to displays 82, 84 and 86 of control panel 66, indicator panel 88, audio annunciator 90 and to pump drive motor 98. In addition, when sequence valve 18 is connected to pump 12 and a piggyback operation has been selected, pump control 94 provides the valve control signal to sequence valve 18.

Control panel 66 allows the medical personnel to "set up" an IV administration schedule so that predetermined volumes of the primary and secondary solutions are delivered at predetermined rates. Pump control 94 controls the operation of both sequence valve 18 and pump drive motor 98, so that it controls both the particular solution being pumped at any given time, and the rate at which the fluid is being pumped.

By depressing STBY key pada 70, the medical personnel places pump 12 in a standby mode. This allows changing or resetting of both rates and volume limits for both the primary and piggyback solutions. The primary solution rate is selected by depressing PRIMARY key pad 72 and then RATE key pad 76, followed by the keys representing the numerical value desired. The primary volume limits can then be set by pressing LIMIT key pad 78 and then using the numerical keys to enter the desired numerical limit for the primary solution.

For the piggyback or secondary solution, PIGGYBACK key pad 74 is pressed. RATE key pad 76 is then pressed, followed by appropriate numerical keys to enter the piggyback rate. LIMIT key pad 78 is then depressed, followed by selected numerical key pads to set the piggyback volume limit.

Pump control 94 stores the rates and volume limits entered for both the primary solution and the piggyback solution. These stored values are used, together with an accumulated volume infused value in controlling sequence valve 18 as well as pump drive motor 98.

In a preferred embodiment of the present invention, sequence valve 18 is a spring loaded, solenoid actuated device which initially occludes primary tubing 30 so that the secondary solution is pumped first. Sequence valve 18 is placed in this initial condition by inserting primary tubing 30 into one slot of sequence valve 18 and then cocking lever 100 so that primary tubing 30 is occluded. Secondary tubing 40 is then inserted into an adjacent slot alongside primary tubing 30 in sequence valve 18 as shown in FIG. 1.

Operation of pump 12 in the piggyback mode is initiated by depressing OPR key pad 18. Pump control 94 provides pump drive control signals to pump drive motor 98 which cause motor 98 to produce the pumping rate stored for the piggyback solution. As pump drive motor 98 is operated, pump control 94 maintains an accumulated value which represents the amount of secondary solution which has been pumped with sequence valve 18 in its initial setting. When that accumulated value reaches the piggyback volume limit stored by pump control 94, a valve control signal is produced which causes sequence valve 18 to change state. Sequence valve 18, in response to the valve control signal, occludes secondary tubing 40, and allows primary solution to flow through primary tubing 30, to inlet tubing 22. Upon receiving the signal from sequence valve 18 indicating that the change has been made, pump control 94 provides pump drive signals which cause pump drive motor 98 to operate at the pumping rate selected for the primary solution. Pump control 94 again maintains an accumulated value which represents the amount of primary solution which has been pumped. This value is displayed on volume infused display 86. When the accumulated value reaches the stored primary volume limit, pump control 94 halts operation of pump drive motor 98 and provides an indication through indicator panel 88 and audio annunciator 90 that both the piggyback and primary administration has been completed. At that point, the medical personnel responsible for the IV administration are required to intervene to set a new schedule of primary and piggyback rates and volume rates.

The system of the present invention is advantageous because all of the medication for a single day or for several days can be stored in one large secondary bag 16, as opposed to much smaller secondary bags which run dry after each administration of that medication. For example, if a patient is to receive 50 milliliters of secondary medication four times a day, four bags would be required with the prior art systems, in which the switching from the secondary bag to the primary solution is determined by when the secondary bag is empty. With the system of the present invention, one 200 milliliter bag can be used for the entire day. Since a large or a small bag costs essentially the same, there is a cost saving just by virtue of the reduced number of bags. In addition, the system significantly reduces the amount of time which is required for medical personnel. It is not necessary to change the secondary bag 16 after each administration of medication, and in fact the present invention allows the secondary medication to be provided multiple times without a change in the secondary bag.

By use of pump control 94 within housing 54 of pump 12 to control operation of both pump 12 and sequence valve 18, the size, weight, complexity and cost of sequence valve 18 are significantly reduced. As a result, sequence valve 18 can be suspended from the tubing (e.g. primary tubing 30) rather than requiring separate clamping to a pole. This makes sequence valve 18 simpler and easier to use, and makes it portable so that sequence valve 18 can be moved wherever pump 12 is moved.

Figure 4:
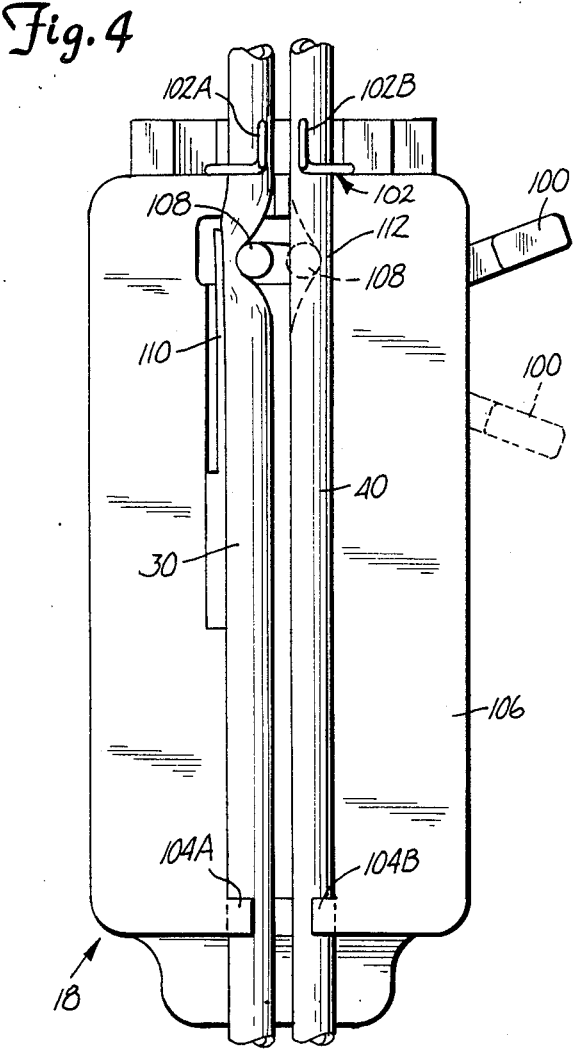
FIG. 4 is a front view of a first preferred embodiment of the sequence valve of the system of FIG. 1.

FIGS. 4 through 7 show a first preferred embodiment of sequence valve 18. FIG. 4 shows valve 18 in its normal initial operating position for piggyback operation. As shown in FIG. 4, tubes 30 and 40 pass side-by-side through valve 18. At the upper end, tubing 30 and tubing 40 are retained by retainer spring 102, which has a pair of retainer arms 102A and 102B. At the lower end, tubing 30 and tubing 40 are retained in side-by-side position by retaining fingers 104A and 104B of front cover 106.

As shown in FIG. 4, lever 100 is in its uppermost ("cocked") position, which causes occluder stud 108 to be in its leftmost position. As a result, primary tubing 30 is pinched off between occluder stud 108 and leaf spring 110. Also shown in phantom in FIG. 4 is the position of lever 100 and the position of occluder stud 108 after sequence valve 18 has received a valve control signal from pump 12 which causes occluder stud 108 to move generally to the right to pinch off secondary tubing 40 between occluder stud 108 and wall 112. Thus sequence valve 18 has two stable positions, one in which primary tubing 30 is occluded and secondary tubing 40 is unoccluded; and the other in which secondary tubing 40 is occluded and primary tubing 30 is unoccluded.

Figure 5:
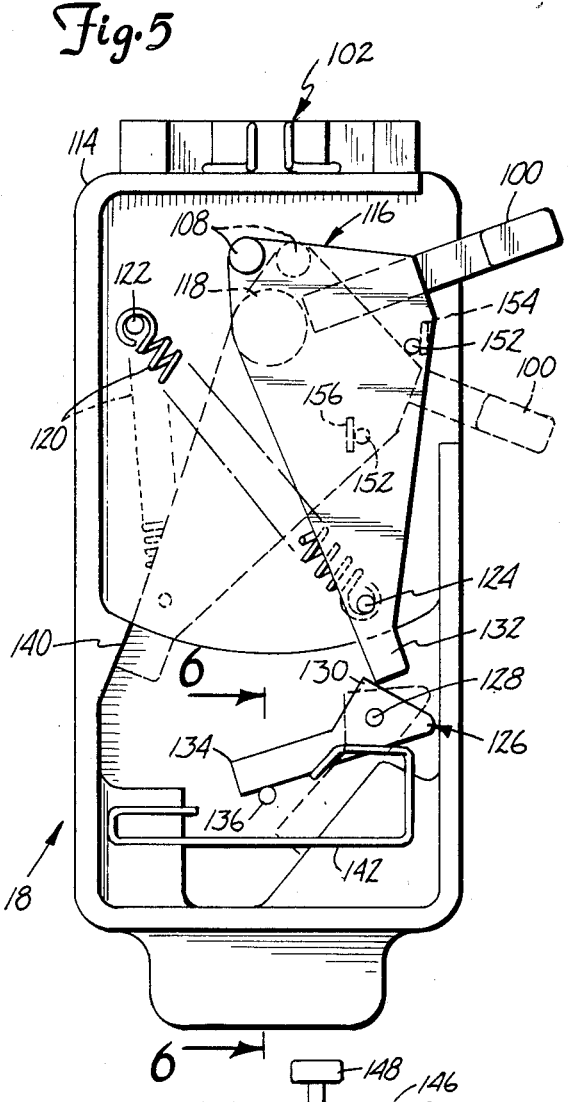
FIG. 5 is a front view of the sequence valve of FIG. 4 with the front cover removed.

FIG. 5 shows sequence valve 18 with front cover 106 removed. The operating mechanisms of sequence valve 18 are supported by valve base 114. Both occluder stud 108 and lever 100 are attached to bell crank 116, which is pivotally mounted to valve base 114 by pivot pin 118.

As in FIG. 4, two positions of occluder stud 108 and the other moving parts of sequence valve 18 are shown. Solid lines represent the initial position in which primary tubing 30 is occluded, and phantom lines to illustrate the second position in which secondary tubing 40 is occluded.

Bell crank 116 is biased in a clockwise direction by bias spring 120, which is connected at its upper end to stud 122 and thus to valve base 114, and which is connected at its lower end to stud 124 which projects rearwardly from the lower end of bell crank 118.

Latch 126 is pivotally mounted about pivot pin 128, and has a latch tooth 130 which engages lower leg 132 of bell crank 116 when lever 116 is its cocked upper position. Latch arm 134 is held in the initial position by solenoid plunger 136, which prevents rotation of latch 126 about the axis defined by pivot pin 128.

Figure 6:
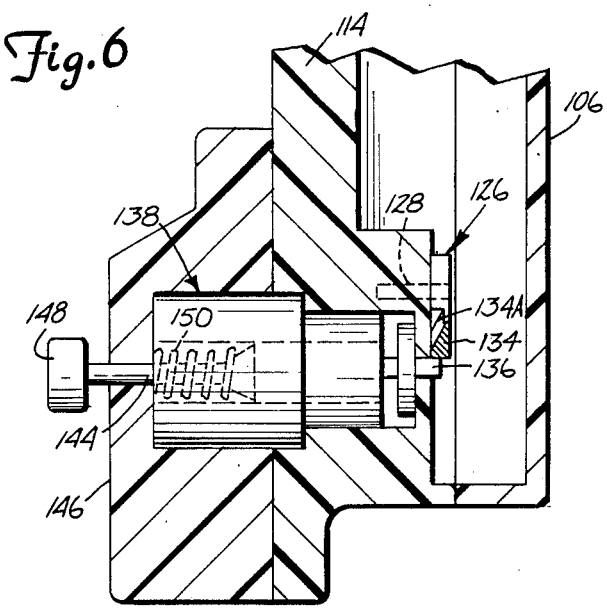
FIG. 6 is a sectional view along section 6—6 of FIG. 5.

Valve 18 will remain in a stable initial position until a valve control signal actuates solenoid 138 (FIG. 6). This causes solenoid plunger 136 to be pulled in a rearward direction out of contact with arm 134 of latch 126. This allows the bias force of spring 120 to rotate bell crank 116 and in turn latch 126 about their respective pivot pins 118 and 128 to the position shown in phantom in FIG. 5. The second stable position of bell crank 116 is defined by stop 140, which engages leg 132 of bell crank 116 to prevent further rotation in the clockwise direction. In this second stable state, occluder stud 108 is at its rightmost position, so that secondary tubing 40 is pinched off between occluder stud 108 and wall 112.

Sequence valve 18 is reset to its initial position by moving lever 100 upwards to the initial cocked position shown in solid lines. Latch spring 142 urges latch 126 back to its initial position when sequence valve 18 is being reinitialized. As shown in FIG. 6, rear surface 134A of arm 134 is bevelled to form a ramp which allows arm 134 to move past solenoid plunger 136 as lever 100 is being cocked.

Solenoid 138 includes a solenoid plunger stud 144 which extends out the rear end of solenoid cover 146. At the rear end of solenoid plunger stud 144 is solenoid button 148. This button allows the nurse or technician to pull solenoid plunger 136 out of the way of latch 126 in order to manually release lever 100, bell crank 116 and latch 126 from the cocked position. Button 148 can then be released and, due to the bias force of bias spring 150, solenoid plunger 136 returns to its normal position shown in FIG. 6.

It is also preferable for sequence valve 18 to provide an electrical signal which indicates the current state of sequence valve 18. In the embodiment shown in FIG. 5, a metal contact stud 152 is attached to bell crank 116. When valve 18 is in its initial state, contact stud 152 is in contact with contact wire 154. When the valve control signal has been received and bell crank 116 has rotated to the position shown in phantom, contact stud 152 has moved into engagement with contact wire 156. Depending upon which wire 154 or 156 is in contact with contact stud 152, a different electrical signal is supplied through cable 152 to pump 12. This provides a simple, yet very effective way of indicating the state of sequence valve 18 to pump 12.

Figure 7:
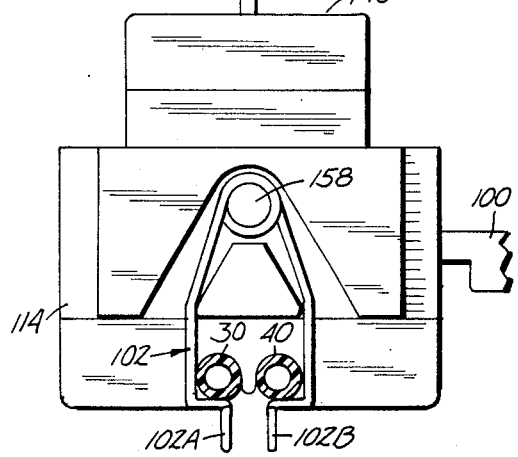
FIG. 7 is a top view of the valve of FIG. 4.

As shown in FIG. 7, upper retainer 102 is preferably a single wire clip which mounts over stud 158 at the upper end of valve base 114. The resilient nature of retainer 102 allows the retainer arms 102A and 102B to be displaced outwardly while tubing 30 and 40 are inserted into sequence valve 18. Once released, arms 102A and 102B return to their normal position shown in FIG. 7, thus securely holding tubing 30 and tubing 40 in place.

Sequence valve 18 shown in FIGS. 4–7 is particularly advantageous, since it is small, light-weight (so that it can be supported on tubing 30 and 40 without the need for a separate support stand) and uses a small, low-power solenoid. By using a pivoted latch 126 and a pivoted bell crank 116, both of which provide a substantial mechanical advantage (e.g. 4:1 each), a very small movement of solenoid plunger 136 provides the sufficient force to move occluder stud 108 to the right so as to pinch off tubing 40. The force required to move solenoid plunger 136 is, for example, only one-sixteenth of the force applied by occluder stud 108 to tubing 40.

Sequence valve 18 shown in FIGS. 4–7 also uses an extremely simple mechanism to pinch off alternately either tubing 30 or tubing 40. By the use of leaf spring 110 to urge tubing 30 toward occluder stud 108, sequence valve 18 does not require a precise alignment of both positions of occluder stud 108, and variations in the diameters of tubing 30 and 40 are accommodated. It is merely necessary to ensure that occluder stud 108 moves far enough to the right to pinch off tubing 40 against right wall 112 for the minimum expected diameter of tubing 40.

FIGS. 8–12 show a second embodiment of the sequence valve (which is designated as valve 18'). This second embodiment is generally similar to the embodiment of sequence valve 18 shown in FIGS. 4–7, and similar reference numerals are used to designate similar elements. The internal operation of the bell crank, latch and solenoid of sequence valve 18' of FIGS. 8–12 are identical to those shown in FIGS. 4–7 and will not be discussed again.

Figure 8:
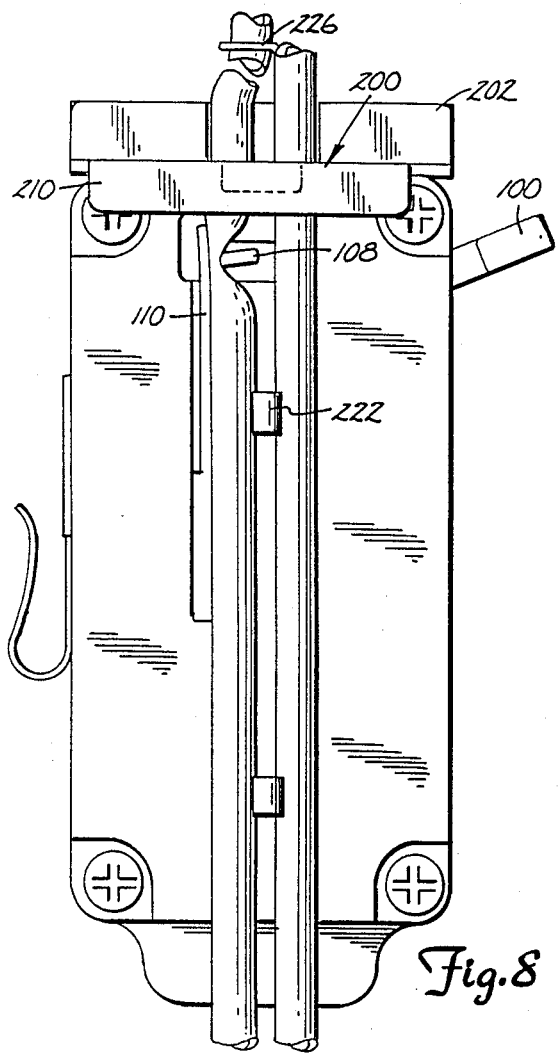
FIG. 8 is a front view of a second preferred embodiment of the sequence valve of the system of FIG. 1.
Figure 9:
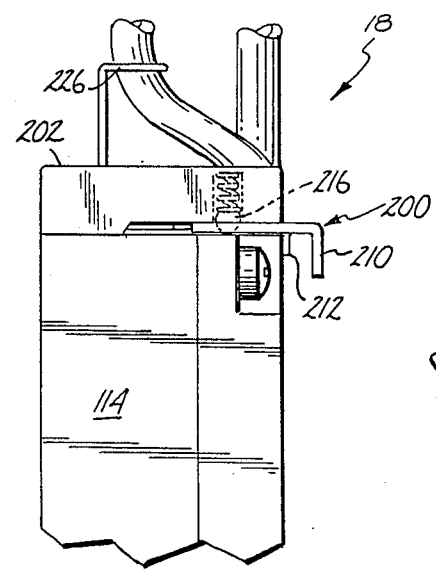

The main difference between sequence valve 18' of FIGS. 8–12 and sequence valve 18 of FIGS. 4–7 is in the retaining of tubing 30 and 40. In sequence valve 18', a tube retainer 200 is pivotally mounted at the upper end of valve 18' between top end plate 202 and the upper ends of front cover 106 and valve base 114. Tube retainer 200 has a right leg 204 which is pivotally mounted about pivot pin 206, a left leg 208, a front flange 210, and a tube hold-down flange 212. The closed position of tube retainer 200 is shown in FIGS. 8–10, and the open position is shown in FIG. 11. Flange 210 forms a handle by which the nurse can pivot tube retainer 200 to the open position to allow insertion or removal of tubing 30 and 40 from sequence valve 18'.

Left leg 208 of tube retainer 200 contains a hole 214 which receives a spring loaded ball 216 mounted in top plate 202 when tube retainer 200 is in the closed position shown in FIGS. 8–10. Spring loaded ball 216 maintains tube retainer 200 in the closed position and prevents it from moving from the closed position if IV pump 12 or tubing 30 or 40 are moved or bumped inadvertently.

Sequence valve 18' also uses tube retainer 200 as a switch to indicate to pump 12 that sequence valve 18' is in a condition to operate. For this purpose, tube retainer 200 is an electrically conductive material, preferably metal. An electrically conductive washer 218, which is partially shown in FIG. 11, is mounted on pivot pin 206 in contact with right leg 204 of tube retainer 200. Spring contact 220 is positioned so that it will be engaged by left leg 208 when tube retainer 200 is in the closed position. Thus when tube retainer 200 is in the closed position, a closed electrical path is provided between conductive washer 218 and spring contact 220.

FIG. 12 shows an electrical schematic diagram of sequence valve 18'. In this embodiment, cable 152 (which connects valve 18' to pump control 94) contains four wires 152A, 152B, 152C and 152D. Solenoid 138 is connected between wires 152A and 152B. Wire 152B is connected to ground. When pump control 94 causes a voltage to be present between wires 152A and 152B, solenoid 138 is actuated.

Wires 152C and 152D are used to indicate to pump control 94 the condition or state of sequence valve 18'. The switch formed by tube retainer 200, conductive washer 218 and spring contact 220 is connected in series with a switch formed by contact stud 152 and contact wire 154 and 156. Contact wire 154 is connected to wire 152D, and contact wire 156 is connected to wire 152C.

If tube retainer 200 is in its open position, both wires 152C and 152D will indicate an open circuit. When tube retainer 200 is closed, normally one of the two wires 152C and 152D will be an open circuit, while the other will be connected to ground. By monitoring wires 152C and 152D, therefore, pump control 94 can determine the operating state of sequence valve 18', as well as whether tube retainer 200 is in closed position.

FIGS. 8–11 also show retainer posts 222 and 224, which are positioned along the channel, and which maintain tubing 30 and 40 in position along the entire length of the channel.

At the upper end of valve 18' is hook 226, which is attached by screw 228 to top plate 202. Primary tubing 30 is threaded through hook 226 to maintain sequence valve 18' in a generally vertical position. This counteracts the tendency of the lower end of valve 18' to tip forward due to the greater weight of solenoid 138 within solenoid housing 146 (see FIG. 6).

Also included in sequence valve 18' is a spring clip 230 and retainer pad 232 which are positioned along the left side of sequence valve 18'. Clip 230 allows sequence valve 18' to be clipped onto pump 12 when not in use. Pad 232 prevents sequence valve 18' from slipping when it is clipped onto pump 12.

Although the present invention has been described with reference to preferred embodiments, workers skilled in the art will recognize that changes may be made in form and detail without departing from the spirit and scope of the invention. For example, although the present invention has been described in the context of a system in which a primary and only one secondary bag are used, it is also applicable to more complex systems in which multiple secondary bags are used in conjunction with a primary bag.

Similarly, although the present invention has been described in the context of a specific type of IV pump sold by applicant's assignee, the present invention is applicable to other IV pump and controller systems as well.

What is claimed is:
1. An IV administration system comprising:
a first source of a first IV fluid;
a second source of a second IV fluid;
an IV control device having an inlet and an outlet for delivering IV fluids at a rate determined by a rate control signal and having a housing;
a first flexible tube having a first end connected to the first source;

a second flexible tube having a first end connected to the second source;

a connector for connecting second ends of the first and second flexible tubes to the inlet of the IV control device;

valve means positioned between the first and second sources and the connector and having the first and second flexible tubes passing therethrough for controlling fluid flow from the first and second sources to the inlet of the IV control device without contacting the first and second IV fluids, the valve means being manually settable to a first state in which the first tube is pinched off and the second tube is not, and being responsive to a valve control signal to change to a second state in which the second tube is pinched off and the first tube is not wherein the valve means maintains one of the tubes in a pinched off condition at all times; and wherein the valve means is normally deenergized in both its first and second states and is energized in response to the valve control signal to switch from the first to the second state;

means for connecting the outlet of the IV control device to a patient; and control means located within the housing for providing the rate control signal and the valve control signal to cause the IV control device to deliver the first IV fluid to the patient at a first rate until a first predetermined volume has been delivered and the second IV fluid to the patient at a second rate until a second predetermined volume has been delivered.

2. The IV administration system of claim 1 and further comprising:

means for providing input signals to the control means which select the first and second rates and the first and second predetermined volumes.

3. The IV administration system of claim 1 wherein the control means comprises:

means for maintaining an accumulated volume value based upon operation of the IV control device which represents a volume of fluid which has been delivered;

means for providing the valve control signal based upon a relationship between the accumulated volume value and the first predetermined volume when the first IV fluid is being delivered and based upon a relationship between the accumulated volume value and the second predetermined volume when the second IV fluid is being delivered.

4. An IV administration system for administering a plurality of IV fluids to a patient, the system comprising:

first and second sources of IV fluid, each source providing a different IV fluid;

an IV control device having an inlet and an outlet for delivering IV fluid;

a connector having first and second inlets and having an outlet connected to the inlet of the IV control device, first and second flexible tubes connecting the first and second sources, respectively, to the first and second inlets of the connector;

valve means positioned between the sources and the connector and having the first and second tubes passing therethrough for controlling fluid flow from the first and second sources to the inlet of the IV control device without contacting the first and second IV fluids, the valve means being manually settable to a first state in which the first tube is pinched off and the second tube is not, and being responsive to a valve control signal to change to a second state in which the second tube is pinched off and the first tube is not wherein the valve means maintains one of the tubes in a pinched off condition at all times; and wherein the valve means is normally deenergized in both its first and second states and is energized in response to the valve control signal to switch from the first to the second state;

means for connecting the outlet of the IV control device to a patient; and control means located within the IV control device for providing the valve control signal to the valve means as a function of volume delivered by the IV control device to cause the IV control device sequentially to deliver predetermined volumes of each of the IV fluids.

5. The IV administration system of claim 4 and further comprising:

means for providing input signals to the control means which select the predetermined volumes.

6. The IV administration system of claim 4 wherein the control means comprises:

means for maintaining an accumulated volume value based upon operation of the IV control device which represents a volume of fluid which has been delivered;

means for providing the valve control signal based upon a relationship between the accumulated volume value and the predetermined volume for the IV fluid being delivered.

* * * * *